US008722103B2

(12) United States Patent
Morris et al.

(10) Patent No.: US 8,722,103 B2
(45) Date of Patent: May 13, 2014

(54) ZEOLITES FOR DELIVERY OF NITRIC OXIDE

(75) Inventors: Russell Edward Morris, Gauldry (GB); Paul Stewart Wheatley, Kirkcaldy (GB); Anthony Robert Butler, St. Andrews (GB)

(73) Assignee: University Court of the University of St. Andrews, St. Andrews (GB)

( * ) Notice: Subject to any disclaimer, the term of this patent is extended or adjusted under 35 U.S.C. 154(b) by 1694 days.

(21) Appl. No.: 10/562,401

(22) PCT Filed: Jul. 5, 2004

(86) PCT No.: PCT/GB2004/002905
§ 371 (c)(1),
(2), (4) Date: Apr. 5, 2006

(87) PCT Pub. No.: WO2005/003032
PCT Pub. Date: Jan. 13, 2005

(65) Prior Publication Data
US 2006/0269620 A1 Nov. 30, 2006

(30) Foreign Application Priority Data

Jul. 3, 2003 (GB) .................................. 0315540.5
Nov. 22, 2003 (GB) .................................. 0327222.6

(51) Int. Cl.
*A61K 33/06* (2006.01)
*A61K 33/00* (2006.01)
(52) U.S. Cl.
USPC ......................................... 424/684; 424/718
(58) Field of Classification Search
None
See application file for complete search history.

(56) References Cited

U.S. PATENT DOCUMENTS

| 3,140,249 | A |   | 7/1964 | Plank et al. |
| 4,775,585 | A |   | 10/1988 | Hagiwara et al. |
| 4,954,526 | A |   | 9/1990 | Keefer |
| 5,492,883 | A | * | 2/1996 | Wu ............................... 502/439 |
| 5,723,110 | A |   | 3/1998 | Yamamoto et al. |
| 5,814,666 | A | * | 9/1998 | Green et al. .................. 514/611 |
| 5,965,264 | A |   | 10/1999 | Barenberg et al. |
| 6,103,275 | A |   | 8/2000 | Seitz et al. |
| 6,110,453 | A | * | 8/2000 | Keefer et al. .............. 424/78.27 |
| 2001/0009831 | A1 |   | 7/2001 | Schink et al. |
| 2002/0054919 | A1 |   | 5/2002 | Hochwalt et al. |
| 2002/0094985 | A1 |   | 7/2002 | Herrmann et al. |
| 2003/0133990 | A1 |   | 7/2003 | Hursey et al. |
| 2006/0032763 | A1 |   | 2/2006 | Herman |

FOREIGN PATENT DOCUMENTS

| EP | 1159972 A2 | 12/2001 | |
| JP | 08092051 A * | 4/1996 | ............... A61K 7/32 |
| WO | WO 95/24908 A1 | 9/1995 | |

(Continued)

OTHER PUBLICATIONS

Hennebt et al., Reactivity of Nitric Oxide with Nickel Ions in A-type Zeolite, J.C.S. Faraday I, 1980, 76,952-962.*

(Continued)

*Primary Examiner* — Melvin C Mayes
*Assistant Examiner* — Stefanie Cohen
(74) *Attorney, Agent, or Firm* — Susan T. Evans; McDermott Will & Emery LLP (57) ABSTRACT

There is described zeolites containing releasably adsorbed nitric oxide, methods of preparing the zeolites, methods of releasing the nitric oxide into a solution or into air and uses of the zeolites in therapy.

19 Claims, 5 Drawing Sheets

(56) References Cited

FOREIGN PATENT DOCUMENTS

| WO | WO 99/30580 A1 | 6/1999 | | |
|---|---|---|---|---|
| WO | WO 99/39574 | 8/1999 | | |
| WO | WO 00/64506 A1 | * | 11/2000 | .............. A61L 31/02 |
| WO | WO 01/21148 A1 | 3/2001 | | |

OTHER PUBLICATIONS

Lunsford "Surface Interactions of NaY and Decationated Y Zeolites with Nitric Oxide as Determined by Electron Paramagnetic Resonance Spectroscopy", *The Journal of Physical Chemistry* 72:12 pp. 4163-4168 (1968).

Pavelic et al. Immunostimulatory Effect of Natural Clinoptilolite as a Possible Mechanism of Its Antimetastatic Ability, *J. Cancer Res. Clin. Oncol.* 128:1 pp. 37-44 (2002).

Rudolf et al. "Adsorption and Desorption Behavior of NO on H-ZSM-5, Na-ZSM-5, and Na-A as Studied by EPR", *J. Magnetic Resonance* 155:1 pp. 45-56 (2002).

Sasaki et al. "Effect of Iron Modification on the Adsorption Property of Nitrogen Monoxide on Zeolite Y", *J. Ceram Soc. Jpn* 106:1229 pp. 78-83 (1998).

Zhang et al. "Removal of Nitrogen Monoxide on Copper Ion-Exchanged Zeolites by Pressure Swing Adsorption", *Am. Chem. Soc.* 9:9 pp. 2337-2343 (1993).

Zhang et al. "Reversible and Irreversible Adsorption of Nitrogen Monoxide on Cobalt Ion-Exchanged ZSM-5 and Mordenite Zeolites at 273-523 K", *J. Chem. Soc.* 91:4 pp. 767-771 (1995).

International Search Report corresponding to PCT/GB04/002905 mailed on Nov. 10, 2004.

Arai et al. "Removal of $NO_x$ Through Sorption-Desorption Cycles Over Metal Oxides and Zeolites", *Catalysis Today* 22:97-109 (1994).

Cheetham et al. "A Study of Si,Al Ordering in Thallium Zeolite-A by Powder Neutron Diffraction", *Nature* 299:24-26 (1982).

M. Davis "Ordered Porous Materials for Emerging Applications", *Nature* 417:813-821 (2002).

Frank et al. "Nitric Oxide Drives Skin Repair: Novel Functions of an Established Mediator", *Kidney International* 61:882-888 (2002).

L. Ignarro "Biosynthesis and Metabolism of Endothelium-Derived Nitric Oxide", *Annu. Rev. Pharmacol. Toxicol.* 30:535-560 (1990).

Joyner et al. "Preparation, Characterization, and Performance of Fe-ZSM-5 Catalysts", *J. Phys. Chem. B* 103:5963-5976 (1999).

L. Keefer "Thwarting Thrombus", *Nature Materials* 2:357-358 (2003).

Maragos et al. "Complexes of NO with Nucleophiles as Agents for the Controlled Biological Release of Nitric Oxide Vasorelaxant Effects", *J. Med. Chem.* 34:3242-3247 (1991).

Megson et al. "Therapeutic Potential of S-Nitrosothiols as Nitric Oxide Donor Drugs", *Scot. Med. J.* 42:88-89 (1997).

Morrell et al. "Structural Investigation of Silicalite-I Loaded with *n*-Hexane by X-ray Diffraction, Si-29 MAS NMR, and Molecular Modeling", *Chem. Mater.* 14:2192-2198 (2002).

Pluth et al. "Accurate Redetermination of Crystal Structure of Dehydrated Zeolite. Absence of Near Zero Coordination of Sodium. Refinement of Si,Al-Ordered Superstructure", *J. Am. Chem. Soc.* 102:4704-4708 (1980).

Robson et al. "Verified Synthesis of Zeolitic Materials", *International Zeolite Associate*, $2^{nd}$ Revised Ed. (2001).

Shabani et al. "Enhancement of Wound Repair with a Topically Applied Nitric Oxide-Releasing Polymer", *Wound Repair and Regeneration* 4(3):353-361 (1996).

Witte et al. "Nitric Oxide Enhances Experimental Wound Healing in Diabetes", *Br. J. Surg.* 89:1594-1601 (2002).

Works et al. "Photochemical Nitric Oxide Precursors: Synthesis, Photochemistry, and Ligand Substitution Kinetics of Ruthenium Salen Nitrosyl and Ruthenium Salophen Nitrosyl Complexes", *Inorg. Chem.* 41(14):3728-3739 (2002).

Yahiro et al. "Copper Ion-Exchanged Zeolite Catalysts in $deNO_x$ Reaction", *Appl. Catal. A* 222:163-181 (2001).

Notification of Transmittal of the International Preliminary Report on Patentability corresponding to PCT/GB2004/002905 mailed Jan. 24, 2006.

Klier, Kamil, et al., "No Decomposition in Non-Reducing Atmospheres," Technical Progress Report for the Period Dec. 1995-Feb. 1996, prepared for the United States Department of Energy-Pittsburgh Energy Technology Center, Mar. 1996, pp. 1-14.

Zhang et al., "No Adsorbability of Metal Ion-Exchanged Molecular Sieve," Chemical Journal of Chinese Universities, Dec. 1997, pp. 1-6, vol. 18—No. 12.

* cited by examiner

ZEOLITES FOR DELIVERY OF NITRIC OXIDE

RELATED APPLICATIONS

This application claims priority under 35 U.S.C. §371 from PCT Application No. PCT/GB04/002905, filed in English on Jul. 5, 2004, which claims the benefit of Great Britain Application Serial No. 0315540.5 filed on Jul. 3, 2003, and Great Britain Application Serial No. 0327222.6 filed on Nov. 22, 2003, the disclosures and contents of which are incorporated by reference herein in their entireties.

FIELD OF INVENTION

The present invention relates to zeolites containing releasably adsorbed nitric oxide, methods of preparing these zeolites, methods of releasing the nitric oxide into a solution or into air, and uses thereof.

BACKGROUND OF THE INVENTION

Nitric oxide (the chemical formula is NO) is a remarkable small molecule that is vitally important in many biological processes. It is a vasodilator that increases blood flow through arteries and veins, and is also an important factor in controlling/preventing platelet adhesion and aggregation and thrombus formation. It also plays a crucial role in the immune system and in neurotransmission. Much is now known about the mode of action of nitric oxide and it is clear that it has enormous potential in medicine and biotechnology in both in vivo and ex vivo applications.

The controlled delivery of nitric oxide may be important in prophylactic and therapeutic procedures and application. For example, nitric oxide can prevent thrombosis and restenosis following balloon angioplasty and stent insertion in blocked arteries (International Patent Application WO 95/24908). Because nitric oxide is active in many biological processes, targeted delivery is desirable however. The delivery of nitric oxide to the skin may also have therapeutic benefits for patients with peripheral circulatory problems which can occur in conditions such as arthritis and Raynaud's syndrome. Nitric oxide also exhibits antibacterial properties and incorporation into antibacterial devices and use for the treatment of bacterial infections is desirable. Nitric oxide also plays a part in wound healing and angiogenesis, and delivery of nitric oxide to wounds and ulcers can be beneficial when healing is slow which can occur, for example, in elderly patients (M. Shabani et al, Enhancement of wound repair with a topically applied nitric oxide-releasing polymer *Wound repair and regeneration*, 4, 353, 1996 and S. Frank H. Kampfer, C. Wetzler, J. Pfeilschifer, Nitric oxide drives skin repair: Novel functions of an established mediator *Kidney International*, 61, 882, 2002).

However the delivery of nitric oxide to the desired area, and in the required optimum dose is often difficult because nitric oxide is a gas. Delivery of nitric oxide is difficult in both ex vivo e.g. biotechnology applications and in vivo e.g. medical applications.

Various methods of nitric oxide delivery are known such as
(a) molecules which release NO spontaneously;
(b) molecules which are metabolised to give NO;
(c) molecules that release NO on photoactivation;
(d) release of NO from polymers and polymer coatings;
(e) production of NO from a chemical reaction.

The class (a) molecules include molecules known as nitric oxide nucleophile complexes (NONOates) (C. M. Maragos et al, Complexes of NO with nucleophiles as agents for the controlled biological release of nitric-oxide-vasorelaxant effects *J. Med. Chem*, 34, 3242, 1991). These are a variety of molecules which give off nitric oxide spontaneously and have been shown to have a possible use in therapeutic applications (U.S. Pat. No. 4,954,526). However the use of NONOates in therapy is limited because they become distributed throughout the body which may compromise selectivity. The by-products following the release of NO may also form carcinogenic secondary nitrosamines. Other class(a) molecules include nitrosothiols (Megson, I. L., Greig, I. R., Butler, A. R., Gray, G. A. & Webb, D. J. Therapeutic potential of S-nitrosothiols as nitric oxide donor drugs *Scot. Med. J.* 42, 88, (1997)). Also, the class(a) molecules may cause dangerous lowering of systemic blood pressure.

The class (b) molecules include glyceryl trinitrate and sodium nitroprusside (L. J. Ignarro Biosynthesis and metabolism of endothelium-derived nitric-oxide *Ann. Rev. Pharmacol. Toxicol.* 30, 535, 1990). These compounds are currently widely used as vasodilators, however prolonged use can lead to toxic side products such as cyanides. Furthermore, tolerance can be displayed because these molecules need to be metabolised to release NO. The targeting of NO to particular sites may also be poor resulting in the effects tending to be systemic.

The class (c) molecules require specific activation, for example, light having a specific wavelength which can be difficult to initiate (C. Works, C. J. Jocher, G. D. Bart, X. Bu, P. C. Ford, Photochemical Nitric Oxide Precursors *Inorg. Chem.*, 41, 3728, 2002).

Class (d) release of nitric oxide mitigates the problems associated with systemic activity by delivering nitric oxide to a specific target site by supporting a nitric oxide releasing compound on a solid article. Such NO releasing compounds may be polymeric materials which can be coated onto medical instruments which can be used to target specific areas of the body for treatment. The polymers may contain, for example, the $N_2O_2$ group that releases NO after a chemical reaction (International Patent Application WO 95/24908 and US Patent Application 2002094985). However, the release of NO in such circumstances can be difficult to control and currently the preparation of the required materials may be expensive, often requiring multi-step processes and presenting difficult storage problems because of instability at room temperature and require storage at a cold temperature. The possible use of such polymers has been shown in the treatment of cardiovascular problems, for example, restenosis; the manufacture of anti-thrombogenic medical devices; alleviation of abnormal vasconstriction in the blood supply of the skin (Reynaud's syndrome) and for wound healing.

Class (e) delivery of nitric oxide has been proposed for topical applications by releasing nitric oxide from a chemical reaction. The chemical reaction involves the application of sodium nitrite, ascorbic acid and maleic acid, which gives off NO when contacted by water (U.S. Pat. No. 6,103,275). However, this reaction takes place only in acidic conditions and so may cause irritation, especially to sensitive skin of elderly patients. Additionally, the nitric oxide is released as a short-lived burst rather than in a controlled manner.

The object of the present invention is to obviate and/or mitigate the problems of nitric oxide storage and delivery.

SUMMARY OF THE INVENTION

According to a first aspect of the present invention there is provided a zeolite material comprising releasably adsorbed nitric oxide.

Zeolite materials are a class of aluminosilicate materials which are known and used in a number of applications, for example, ion exchange, gas separation and catalysis (A. Dyer, An Introduction to Zeolite Molecular Sieves, J. Wiley and Sons, 1988).

According to a second aspect of the present invention there is provided a method of preparing a zeolite material which comprises releasably adsorbed nitric oxide, said method comprising the steps of providing a zeolite material and contacting said material with nitric oxide gas.

Zeolites which are suitable for the present invention may be either naturally found or synthetically made. The zeolites contain pores and channels having dimensions which allow small molecules or ions to be adsorbed onto the internal surfaces of the material. The general formula of a zeolite framework is $Al_y Si_{1-y} O_4^{y-}$. For each aluminium atom in the zeolite framework, one negative charge is introduced which must be balanced by an extra-framework cation. These cations can be inorganic or organic in nature, and can be exchanged using standard ion exchange processes (M. E. Davis, Ordered porous materials for emerging applications *Nature* 417, 813, 2002).

The zeolites may comprise transition element cations as the extra-framework species e.g. iron, copper, ruthenium, and such zeolites can adsorb nitric oxide to form complexes inside the cavities of the zeolite material. These complexes are strong and may enable the nitric oxide to be stored until needed. Cations of other elements, for example, sodium and potassium bind nitric oxide less strongly. Those skilled in the art may use standard ion exchange processes to introduce the required metal ions into a zeolite structure as extra-framework cations (Plank et. al., U.S. Pat. No. 3,140,249; Preparation, characterisation, and Performance of Fe-ZSM-5 Catalysts R. Joyner and M. Stockenhuber, J. Phys. Chem. B., 1999, 103, 5963-5976). Using such techniques it is possible to incorporate mixtures of cations in the zeolite structures.

The zeolites may be provided in a dehydrated state.

The amount of nitric oxide which may be loaded into the zeolites can be controlled by varying the relative amounts of the extra-framework cations, controlling their chemical nature, and/or the total number of ions present. For example, the number of extra framework cations present in the zeolite structure may depend on the amount of aluminium present in the framework. More aluminium ions require more extra framework cations to balance the negative charge. The extra framework cations may then interact with the NO molecules.

The chemical nature of the extra framework cations may also be changed (for example monovalent cations, e.g. $Na^+$ and $Ag^+$ may be exchanged for divalent cations, e.g. $Fe^{2+}$ and $Cu^{2+}$ or trivalent cations, e.g. $Ru^{3+}$ and $Fe^{3+}$) Each different cation may have a different affinity for NO and changing the cations present in the zeolite framework may be used to control the release of NO. Such manipulation of the zeolite composition can affect the rate at which the nitric oxide is released from the zeolite. For example a sodium-loaded zeolite may bind nitric oxide less strongly than an iron-loaded zeolite to release the nitric oxide more rapidly. A mixed sodium/iron zeolite may release nitric oxide at a different rate to either a sodium-loaded zeolite or an iron-loaded zeolite, and such release of nitric oxide may present a different rate profile.

The choice of zeolite framework can also be used to vary the loading and release rate of nitric oxide. Zeolite frameworks are available in synthetic materials with a variety of different structures, and suitable frameworks may be chosen that offer the desired properties for the application under consideration. For example, the pores and channels in a zeolite structure may be defined by the size of the pore or channel openings. The zeolite with the structure LTA has openings defined by 8 pore tetrahedral units (i.e. a ring of 8Si/Al atoms and 8 oxygen atoms). Zeolite MFI has a larger ring opening defined by 10 tetrahedral units, and FAU by an even larger pore opening of 12 tetrahedral units. The dimensionality of the pores can also differ between zeolite frameworks. For example, some zeolites have channels that run in only one direction (one dimensional channel systems) while others have systems of interacting channels in two or three dimensions (2-dimensional and 3-dimensional channel systems). The size, shape and dimensionality of zeolites may affect the rates of diffusion and adsorption/desorption of NO, and may be used to control the rate of release of NO from the zeolite in a particular application.

Thus, the composition of the zeolite material may be tailored to control the amount of nitric oxide loaded into the zeolite structure and/or the rate at which the nitric oxide is released from the zeolite.

Such zeolite structures may be chosen from, but not limited to, frameworks having the following three letter framework codes: LTA, FAU, MFI, MOR, FER, BEA, PHI and SAS (See International Zeolite Association Website www.iza-online.org for details of how the codes relate to the frame-work structures of the zeolites which is incorporated herein by reference). These three letter codes describe the framework architecture of the zeolites, that is their structure, but do not describe the composition of the zeolite which may vary widely. The three letter codes are used as a nomenclature system for zeolites.

The zeolites which may be used in the present invention may have the following general formula (I):

$$[(M1^{n+})_{x/n}(M2^{p+})_{y/p} \ldots (Mn^{q+})_{v/q}][Al_z Si_{2-z} O_4] \quad (I)$$

wherein M1 and M2 . . . Mn are extra framework metal cations of elements selected from the group consisting of Li, Na, K, Ca, Mg, Fe, Cu, Ru, Rh, Co, Ni, Zn and Ag.
x may range from zero to nz,
y may range from zero to pz, and
v may range from zero to qz,
subject to the condition that x/n+y/p+ . . . +v/q=z.
z is the number of silicon atoms replaced by aluminium atoms in the zeolite framework.
n+, p+ and q+ are the charges of the extra framework metal cations, and may individually take the values of +1, +2 or +3.
M1 and M2 . . . Mn may also be chosen from small organic cations such as $N(R_1)_a(R_2)_b^+$ wherein $R_1$ and $R_2$ are independently selected from H, —$CH_3$, —$CH_2CH_3$, or —$CH_2CH_2CH_3$, and a and b are independently 0, 1, 2, 3 or 4 such that a+b=4;

When M1 and/or M2 are small organic cations, $NH_4^+$ is prefered.

The zeolites which preferably may be used in the present invention have the following general formula (II):

$$[(M1^{n+})_{x/n}(M2^{p+})_{y/p}][Al_z Si_{2-z} O_4] \quad (II)$$

wherein M1 and M2 are as defined previously,
x may range from zero to nz, and
y may range from zero to pz, subject to the condition that x/n+y/p=z.

Prior to nitric oxide loading, the zeolites for use in the present invention may be fully or partially dehydrated, for example, under vacuum to remove water from the zeolite channels. The resulting zeolite may then be exposed to nitric oxide to load the zeolite.

Typically, the nitric oxide loading is performed at a temperature from −100° C. to 50° C.

The loading of nitric oxide may be performed with pure NO or with a mixture of NO and a carrier gas such as an inert gas, for example helium, argon or other inert gas including mixtures thereof.

The loading is typically performed at a pressure above atmospheric pressure, for example from atmospheric pressure up to a pressure of 10 bar.

The nitric oxide loaded zeolites may be sealed inside airtight packaging for storage and transport purposes.

Upon exposure of the nitric oxide loaded zeolite to moisture, for example an aqueous environment such as water or blood, the nitric oxide is displaced from the metal complex inside the zeolite resulting in release of nitric oxide gas into the aqueous environment.

The nitric oxide may also be released from the nitric oxide loaded zeolite when placed in air.

The release of nitric oxide may occur at a variety of temperatures, however room temperature or body temperature is preferred.

The nitric oxide loaded zeolite may be prepared in the form of a powder or a monolith for use for example in topical therapeutic applications or in vitro applications such as delivery of specific amounts of NO to cell cultures. For example, a specific amount of NO may be loaded into a zeolite and then, knowing the extent of release or release profile of the NO loaded zeolite, a precise amount of NO may be delivered to the cell culture. This principle may also be applied to other delivery applications of NO e.g. in therapeutic, cosmetic and/or hygiene, applications so that a specific amount or dose of NO may be administered.

The monoliths may be formed by compression of a zeolite powder or by mixing a powdered zeolite with a suitable binder which is well known in the manufacture of zeolite catalysts.

Suitable binders include, but are not limited to, ceramic binders e.g. silica or alumina, and polymeric binders, e.g. polysulfone, polyethene, PET, polystyrene polytetrafluoroethylene (PTFE) and other polymers.

Alternatively the zeolites may be provided as coatings on medical devices such as metallic or plastics medical devices. The coated devices may then be delivered to the locality where the nitric oxide is required. For example, a zeolite coated stent may be used to perform balloon angioplasty and the release of nitric oxide under these conditions may be used to reduce restenosis.

Typically, the zeolites are provided in a suitable form as discussed above, and then loaded with nitric oxide ready for storage and used at a later time.

A powdered zeolite loaded with nitric oxide may be used in topical applications such as for wound dressing, and may be provided, for example, in a bandage for application to a wound for release of the nitric oxide into the wound to aid healing. A zeolite provided as a monolith may be used e.g. for topical applications or, for example, for suppository application in the treatment of severe constipation.

According to a third aspect of the present invention there is provided a zeolite material comprising releasably adsorbed nitric oxide for use in surgery and/or therapy.

According to a fourth aspect of the present invention there is provided a pharmaceutical, neutraceutical or cosmetic preparation comprising a zeolite material comprising releasably adsorbed nitric oxide together with a pharmaceutical/neutraceutical/cosmetic carrier therefor.

The present invention also provides the use of a zeolite material comprising releasably adsorbed nitric oxide in the preparation of a medicament for use in the treatment or prophylaxis of disease.

Diseases or medical conditions which may be treated include infections of the skin, including dermatophyte fungi, leishmaniasis, molluscum and papilloma virus, and mycobacterium infections. Further uses include therapeutic applications in anti-neoplastic activities, immune response modification, treatment of Raynaud's disease, wound healing and skin pigment modification. Yet further uses include treatment of restonsis, psoriasis and eczema, and skin cancer (melanoma) Therapies for other bacterial problems include the reduction of severe foot or body odour problems, and in the treatment of Methicillin Resistant *Staphylococcus Aureus* infections.

According to a sixth aspect of the present invention there is provided a medical article comprising a zeolite material.

The zeolite material of the medical article may be provided without nitric oxide loaded therein to allow loading with nitric oxide prior to use and/or storage of the medical device ready for subsequent use.

Alternatively, the zeolite material of the medical article may be provided as a zeolite material comprising releasably adsorbed nitric oxide.

Suitable medical articles for use in the present invention include stents, catheters, wound dressings, bandages, self-adhesive plasters and patches.

The beneficial properties of nitric oxide may be advantageously employed in cosmetic and personal hygiene applications.

According to a seventh aspect of the present invention, there is provided use of a zeolite comprising releasably adsorbed nitric oxide in cosmetic and/or personal hygiene applications.

For example the zeolites of the present invention which comprise releasably adsorbed nitric oxide may be used in cosmetic preparations; deodorants; skin preparations such as anti-aging skin preparations and preparations applied before, during or after hair removal by shaving or by application of depilatory preparations; hair preparations; depilatory preparations and the like.

Accordingly, the present invention also provides, as an eighth aspect, a cosmetic and/or personal hygiene product comprising a zeolite which comprises releasably adsorbed nitric oxide.

The present invention also provides, as a ninth aspect, a method of releasing nitric oxide comprising the steps of
 (i) providing a zeolite material comprising releasably adsorbed nitric oxide;
 (ii) contacting said zeolite material with a medium into which said nitric oxide is to be released.

Such release of nitric oxide is preferably achieved in a controlled manner, for example, by providing a suitable zeolite material with an established controlled release profile.

The medium into which the nitric oxide is to be released may be simply air surrounding the nitric oxide loaded zeolite, or may be, for example, an aqueous medium.

The release may be performed either inside an animal body, topically to an animal body or in non-body applications such as release into cell cultures.

The release may be performed at any suitable temperature, however room or body temperature is preferred.

The method of releasing nitric oxide may be applied to the treatment of humans or animals and accordingly the present invention further provides as an tenth aspect a method of treatment or prophylaxis of an individual in need thereof comprising providing a zeolite comprising releasably adsorbed nitric oxide and contacting said zeolite with said individual.

Embodiments of the present invention shall now be described with reference to the following non-limiting examples in which:

Examples 1, 1a and 1b describe the preparation of ion-exchanged zeolites;

Examples 2, 2a and 2b describe the preparation of nitric oxide-loaded zeolites;

Example 3 describes the release of nitric oxide from a nitric oxide loaded zeolite into the atmosphere;

Example 4 describes the release of nitric oxide from a nitric oxide loaded zeolite into solution;

Example 5 describes the release of nitric oxide from an alternative nitric oxide loaded zeolite into the atmosphere;

Example 6 describes the quantification of nitric oxide in solution by direct measurement;

Example 7 describes the release of NO from Co- and Mn-exchanged zeolite-A into wet and dry argon atmospheres;

Example 8 describes the inhibition of platelet aggregation by a NO-loaded zeolite/PTFE disk; and Example 9 describes the antibacterial action of NO-containing zeolites.

Reference in the examples is made to the following figures in which.

EXAMPLE 1

Preparation of Ion-Exchanged Zeolites

The synthesis of zeolites is well known to those with knowledge of the art, and ion exchange of the zeolites can be carried out by standard methods (Plank et. al., U.S. Pat. No. 3,140,249; Preparation, characterisation, and Performance of Fe-ZSM-5 Catalysts R. Joyner and M. Stockenhuber, J. Phys. Chem. B., 1999, 103, 5963-5976). The ion-exchanged zeolite is then dehydrated under vacuum to remove water. Analysis of the zeolites is carried out using elemental analysis, X-ray diffraction and spectroscopic analysis.

EXAMPLE 1a

An example of the preparation of a dehydrated ion-exchanged zeolite is described below.

The zeolite (MFI, 2 g) was placed in a 0.05 M solution of the metal ion (200 ml, distilled water) to be exchanged and stirred for 24 hours. Alternatively, with the same concentrations the exchange could be carried out under dry conditions in an inert atmosphere (argon) with sonication using methanol as a solvent. The products were recovered by filtration/centrifuge.

The concentration of the metal ion solution and time for the exchange can be varied to vary loading of the metal into the zeolite. Specific examples of different metal ions that have been loaded into the zeolites are given in Table 1.

Table 1—Elemental composition of ion-exchanged zeolites prepared using this methodology. The table shows a range of ion exchange behaviour from very low exchange in the case of iron up to over exchange in the case of copper. Initial composition of the zeolite —$(NH_4)_z[Al_zSi_{2-z}O_4]$ where $z=0.13333$ (Si/Al=14)

| Cation (M) | Final Al/M ratio |
|---|---|
| $Fe^{3+}$ | 17.82 |
| $Ni^{2+}$ | 8.42 |
| $Co^{2+}$ | 3.84 |
| $Cu^{2+}$ | 1.50 |

EXAMPLE 1b

Figure 1:
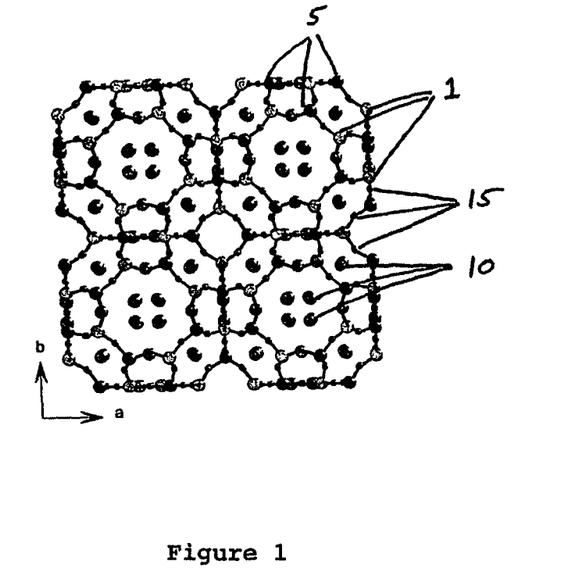
FIG. 1 shows the crystal structure of dehydrated Na-zeolite-A.

Zeolite-A (given the three letter framework code LTA) is a well known material to those skilled in the art, manufactured in greater than 1M tonne amounts annually for use as a detergent builder and water softener. The structure of zeolite-A (Pluth, J. J. & Smith, J. V. Accurate redetermination of crystal structure of dehydrated zeolite A. Absence of near zero coordination of sodium. Refinement of silicon, aluminium-ordered superstructure *J. Am. Chem. Soc.*, 102, 4704 (1980) and Cheetham, A. K., Eddy, M. M., Jefferson, D. A. & Thomas, J. M. A study of Si,Al ordering in thallium zeolite-a by powder neutron-diffraction *Nature*, 299, 24, (1982)) consists of alternating $SiO_4$ and $AlO_4$ tetrahedra that share corners to produce the open framework depicted in FIG. 1, with ion exchangeable cations residing in the channels of the structure. In this case the ion exchangeable cations are shown as sodium cations bound to the oxygen atoms of the framework and can be readily exchanged with transition metal ions. For clarity only the Al—O and Si—O bonds are drawn. The structure labelling in FIG. 1 is as follows: Si=1, Al=5, sodium cations=10 and oxygen atoms=15. Zeolite-A is well known for its affinity to water, often being used (under the name Molecular Sieve 3A, 4A or 5A) to dry solvents in organic chemistry.

Samples of zeolite-A were synthesised according to the procedure given in the *Verified Syntheses of Zeolitic Materials* (Robson H. & Lillerud, K. P. Verified Syntheses of Zeolitic Materials ($2^{nd}$ Revised Edition) international Zeolite Association, (2001); www.iza-synthesis.org). The following ion-exchange procedure was then used to replace the sodium ions in the as-made form with various transition metal cations known to bind nitric oxide strongly ($Mn^{2+}$, $Ni^{2+}$, $Cu^{2+}$, $Co^{2+}$) to give metal ion-exchanged zeolites. Typically, the as-synthesised sodium zeolite-A (5 g) was placed in a 0.05 M solution of the metal acetate (400 ml, distilled water) and stirred for 24 hours. The products were recovered by filtration, washed with distilled water (400 ml) and dried at 100° C. overnight. Elemental analysis was carried out to determine the chemical composition of the zeolites using an Agilent 7500 Series ICP-MS spectrometer. The transition metal zeolite A samples were then dehydrated to remove water.

EXAMPLE 2

Preparation of NO-Loaded Zeolites

Nitric oxide can be produced in situ, or introduced from a cylinder.

EXAMPLE 2a

An example of the preparation of an NO-loaded zeolite is given below.

A 1M asorbic acid solution (200 ml) was degassed by bubbling argon through the solution with stirring. This was then added dropwise to sodium nitrite (~5 g) which had been purged with argon for 30 minutes. A slow flow of argon was used to carry the produced nitric oxide through high surface area potassium hydroxide to remove higher nitrogen oxides, and then through calcium sulfate to dry the gas stream, before being allowed to flow through the ion-exchanged zeolite (e.g., Fe-loaded MFI zeolite ~0.5 g) then finally through a bubbler.

The NO-loaded zeolite is then sealed inside the vessel and stored under the Ar/NO atmosphere (e.g. inside a sealed Schlenk tube at room temperature) until required. The same method of NO-loading can be used for all the zeolites, independent of framework type and ion exchange.

EXAMPLE 2b

Another example of the preparation of NO-loaded zeolite is given below.

The ion-exchanged zeolite-A (~0.3 g) prepared according to Example 1b was dehydrated for 2 hours at 300° C. in vacuo (0.5 mm Hg). This was cooled to room temperature and exposed to approximately 3 atm of a nitric oxide/helium gas mixture (10% NO, 90% He) for 10 minutes, evacuated and exposed again to 3 atm of nitric oxide. This was repeated three times.

For the measurement of NO-release, a flow of argon (either saturated with water vapour or taken directly from the gas cylinder, 5 ml min$^{-1}$) was passed over a known amount of the NO-loaded zeolite. The gas was then bubbled through phosphate buffered saline solution (pH 7.4, 10 ml) in which a previously calibrated nitric oxide electrode (World Precision Instruments, ISO-NO Mark II) was immersed. The concentration of NO was measured over the course of several hours. All experiments were repeated three times and gave reproducible results.

EXAMPLE 3

Release of NO into the Atmosphere from NO-Loaded Fe-MFI Zeolite

Figure 2:
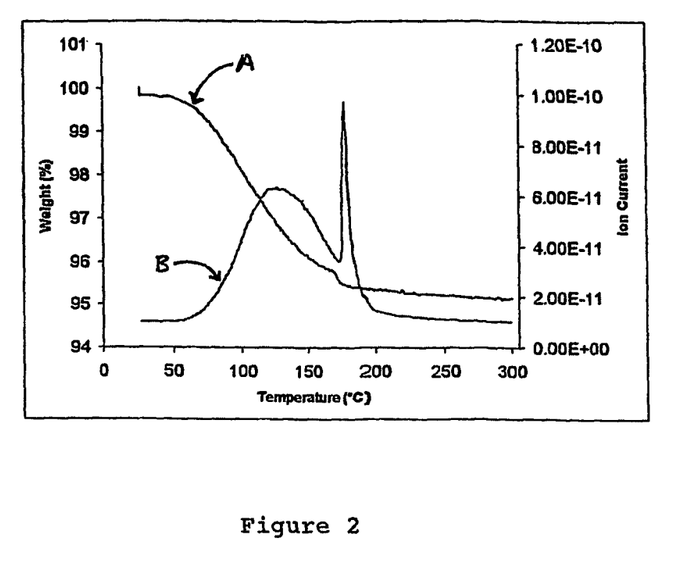
FIG. 2 is a graph showing the release profile of NO into the atmosphere according to Example 3.

Thermogravimmetric analysis coupled with mass spectroscopic analysis of the resultant gases was used to study the temperature dependence of the evolution of nitric oxide from the zeolite. The results are reproduced graphically in FIG. 2 which shows the profile of weight loss (line A) and ion current (line B) for NO in a mass spectrometer versus temperature. NO-loaded Fe-MFI zeolite (0.010 g) was placed in a Netzch Thermogravimmetric analyser coupled to a mass spectrometer. The sample was heated to 300° C. at 10° min$^{-1}$ 48 hours under flowing air and the gases evolved analysed using mass spectrometry. The resultant trace indicated that the amount of NO released increases up to 130° C. before it begins to reduce. However, at ~180° C. a sharp spike in NO production is seen, coinciding with a phase transition in the zeolite sample (confirmed by differential scanning calorimetry). This is the well known monoclinic to orthorhombic phase transition that occurs in zeolite MFI. The phase transition temperature can be altered by careful choice of the silicon to aluminium ratio of the starting zeolite, by controlling the ion exchanged cation and amount, and by controlling the amount of NO loading. Thus property can then lead to a tailored NO release, by for example, a heat pad applied to a wound healing bandage—at temperatures below the phase transition NO release is slow, while above the phase transition NO release is much enhanced. FIG. 1 shows the phase transition at 180° C., but there are literature reports of phase transition in zeolite MFI as low as −100° C. (H Morell, K Angermund, A R Lewis, D H Brouwer, C A Fyfe, H Gies Structural investigation of Silicate-I loaded with n-hexane by X-ray diffraction, Si-29 MAS NMR, and molecular modeling. *Chem. Mater.* 14, 2192, 2002). The precise transition temperature depends on the composition of the zeolite and the loading of NO. Other zeolites, such as FER also show phase transitions that can be tailored in this way.

EXAMPLE 4

Release of NO into Solution from NO-Loaded Fe-MFI Zeolite

Fe-MFI nitric oxide adsorbed sample (0.013 g) was placed in distilled water (10.452 ml) was tested for nitrite (Quantofix Nitrite Sticks) which give a positive result with 20 mg/l $NO_2$. A sample of distilled water was tested for nitrite (as a reference) which resulted in 0 mg/l $NO_2$. Nitrite is formed in solution from the reaction of NO with water and oxygen and is therefore an indirect method for the measurement of NO in solution.

EXAMPLE 5

Release of NO into Atmosphere from NO-Loaded Fe-ZSM-5

Figure 3:
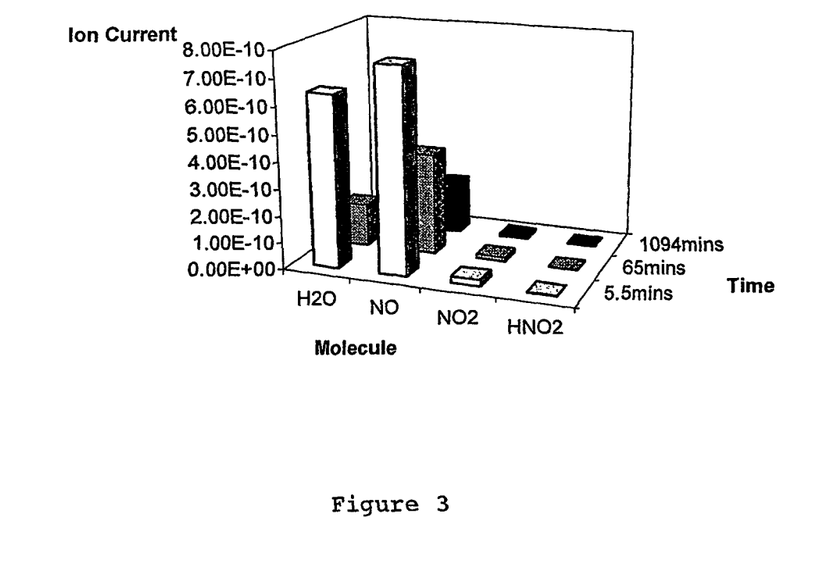
FIG. 3 is a bar chart showing the release profile of NO into the atmosphere at different times according to Example 5.

A small sample of NO-loaded Fe-ZSM-5 (0.010 g) was placed in a Netzch Thermogravimmetric analyser coupled to a mass spectrometer. The sample was heated to 37° C. for 48 hours under flowing air and the gases evolved analysed using mass spectrometry. The resultant trace indicated that NO is slowly released from the zeolite at these temperatures into the atmosphere. FIG. 3 shows the profile of NO released from the zeolite at different times during the cycle. The bar chart shows ion current (from mass spectrometer) versus time for four molecules ($H_2O$, NO, $NO_2$ and $HNO_2$) released from NO-loaded Fe-MFI. It can be clearly seen that NO is the most abundant gas given off at all times.

EXAMPLE 6

Quantification of NO in Solution by Direct Measurement Using a Nitric Oxide Electrode.

The present invention is directed in particular to the delivery of NO above chronic wounds, as animal models have shown that topical application of NO can significantly promote wound closure (Shabnai M., Pulfer S. K., Bulgran J. P. & Smith, D. J. Enhancement of wound repair with a topically applied nitric oxide-releasing polymer. *Wound Rep. Regen.* 4, 353, (1996)) and there is evidence that NO can be used to treat diabetic ulcers (Witte, M. B., Kiyama, T. & Barbul, A, Nitric oxide enhances experimental wound healing in diabetes *Br. J. Surg.*, 89, 1594, (2002)). A useful model for this is the release of NO into a moist atmosphere that is in contact with the liquid phase (phosphate buffered saline pH 7.4). The amount of nitric oxide absorbed by the solution is then measured using a nitric oxide electrode.

The World Precision Instruments ISO-NO Mark II nitric oxide electrode was calibrated using the titration method according to the procedure described by World Precision Instruments (ISO-NO Mark II Instruction Manual, World Precision Instruments, 2002). The metal ion-exchanged zeolite with adsorbed nitric oxide was transferred into a glass tube and wet argon (5 ml min$^{-1}$) was allowed to flow over it. This stream was then directed to bubble through a buffered solution (pH 7.4 at 37° C.) into which the nitric oxide electrode was immersed. Data on the release of nitric oxide was then collected over several hours.

Figure 4:
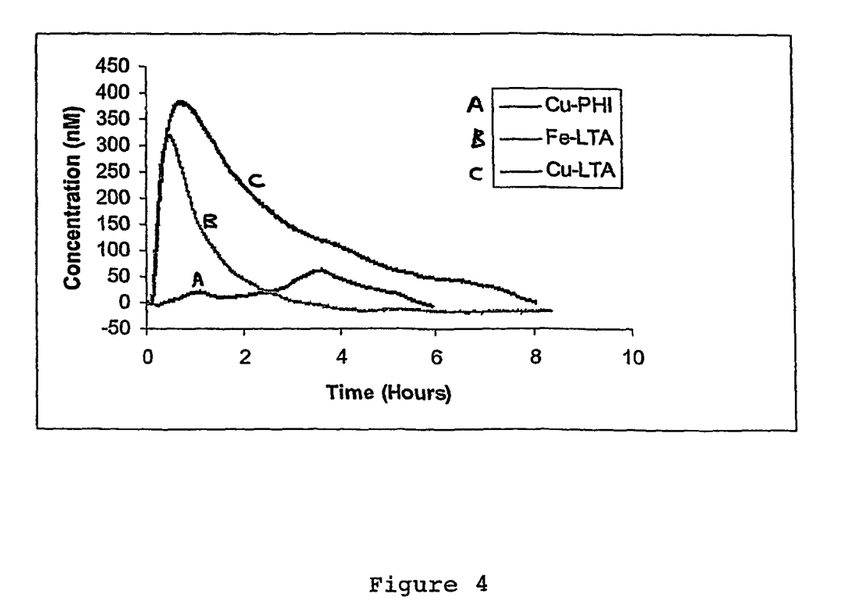
FIG. 4 is a graph which shows the amount of dissolved NO concentration in accordance with Example 6.

FIG. 4 shows the dissolved nitric oxide concentration (not normalised for mass of zeolite or degree of ion exchange) produced when three NO-loaded zeolite samples are exposed to a flow of moist argon as described above. The gas flow is then bubbled through the buffered solution and the nitric oxide concentration measured with time. The experiment measures the uptake of nitric oxide by the solution, and takes no account of loss of nitric oxide that does not dissolve in the liquid. However, for many of the proposed applications (e.g. as a wound-healing bandage) where release of nitric oxide is not directly into a solution, this experiment mimics the situation more closely than would release of the nitric oxide directly into a liquid.

The results illustrate that different nitric oxide-loaded zeolite materials release NO in different ways. Zeolites with the LTA structure release their NO relatively quickly, while those based on the PHI framework release nitric oxide over a much longer timescale. It is noted that the copper and iron ion exchanged LTA zeolites show similar release profiles. The results do show in all cases that the concentration of nitric oxide in the solution is of similar magnitude (nanomolar to micromolar concentrations) to that found in many biological situations.

Figure 5:
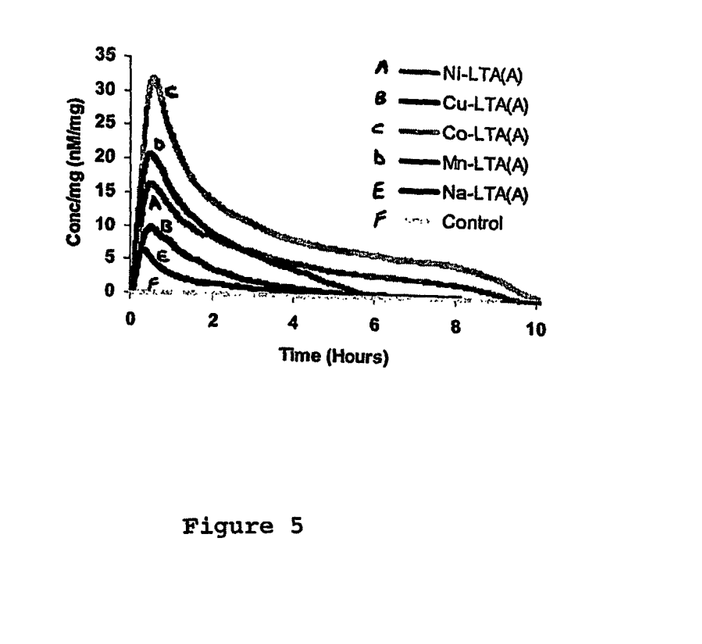
FIG. 5 is a graph showing the release profile of NO into an argon flow in accordance with Example 6.

FIG. 5 shows the NO release profiles measured as described above using a nitric oxide electrode for a number of transition metal exchanged zeolite-A samples in contact with an argon flow that has been saturated with water vapour. The control is a $Co^{2+}$— exchanged zeolite that has not been exposed to nitric oxide. The electrode response results have been normalised to give the concentration of NO in solution per mg of zeolite material. The order of how much NO is released for each different metal agrees well with the NO adsorption properties of transition metal zeolites in pressure swing adsorption studies (Aria, H & Machida, M. Removal of $NO_x$ through sorption-desorption cycles over metal oxides and zeolites *Catal. Today* 22, 97, (1994)). Co-exchanged zeolites releasing the most NO while the original sodium form of the zeolite releases the least NO. It is noted that the copper-exchanged zeolite-A results seem anomalously low, but, without wishing to be bound by theory it is believed that this is because the zeolite is overexchanged, with more copper ions in the channels than is strictly necessary for charge balance reasons. Many of the 'extra' copper ions are probably present as hydroxide species (Yahior, H. & Iwamoto M. Copper ion-exchanged zeolite catalysts in deNO(x) reactions Appl. Catal. A. 222, 163, (2001)) and so reduce the availability of the metal ions for NO coordination.

The cross-over of the $Mn^{2+}$ and $Ni^{2+}$ exchanged zeolites may indicate different distributions of the metal ions between the three possible extra framework cations sites in zeolite-A, some of which may be more susceptible to substitution by water than others.

It is also noted that the release of NO takes place over a relatively long period of time (about 10 hours in FIG. 5), and if there is less water vapour present, the release takes place over an even longer time period.

EXAMPLE 7

NO Release of Co- and Mn-Exchanged Zeolite A into Both 'Wet' and 'Almost Dry' Argon Atmospheres.

Figure 6:
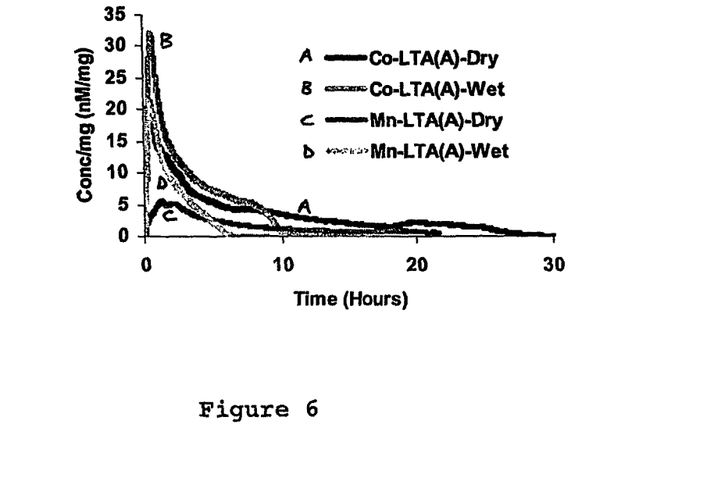
FIG. 6 is a graph showing the release profile of NO from Co- and Mn-exchanged zeolite-A in accordance with Example 7.

FIG. 6 shows the release profile of Co- and Mn-exchanged zeolite A into both 'wet' (water vapour saturated) an d 'almost-dry' argon atmospheres, and in the latter case the zeolites still gave off measurable amounts of nitric oxide more than 24 hours after the experiment began. This shows the importance of water in the mechanism of the No release from these zeolites.

In the 'wet' experiments the argon was bubbled through hot (80° C.) deionised water prior to contacting the zeolite. In the dry experiment the argon was taken directly from the gas cylinder and partially dried over calcium sulphate.

Figure 7:
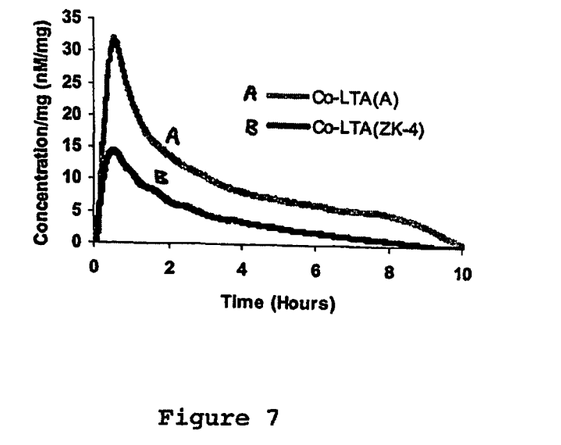
FIG. 7 is a graph showing the release profile of NO from Co-LTA(A) and Co-LTA(ZK-4) zeolites in accordance with Example 7.

The amount of nitric oxide released by the zeolite appears to depend not only on which transition metal is present but also on how much of a particular metal is present. Zeolite-ZK4 is a variant of zeolite-A that has the same framework structure and so has the same framework code (LTA). However, there are fewer exchangeable cations in zeolite-ZK4 as there is aluminium in the framework. This means that there are fewer metal cation sites in the channels of the structure to bind nitric oxide. It can be clearly seen in FIG. 7 that Co-exchanged zeolite-A releases more NO than Co-exchanged zeolite ZK4, consistent with the reduced level of cobalt in the ZK4 structure.

The above experiments indicate the potential of NO-loaded zeolites to deliver nitric oxide into a moist atmosphere for delivery above the skin for applications such as the promotion of wound healing, the treatment of diabetic ulceration or the prevention of bacterial infection. They also illustrate the controllable nature of the NO delivery, which can be changed by varying the type and amount of transition metal present in the zeolite structure.

EXAMPLE 8

Inhibition of Platelet Aggregation

There is a need for improvements in the biocompatibility of materials e.g. for blood contacting solids that are used in vascular grafts and extracorporeal tubing that is necessary in coronary bypass surgery. Life-threatening complications can occur if thrombosis formation (platelet aggregation and adhesion) is induced by materials that are in contact with blood (Keefer, L. K. Thwarting thrombus *Nature Materials*, 2,357, (2003)). Thrombus formation in healthy circulatory systems is inhibited in a number of ways, including the production of small quantities (approximately 1 pmol min$^{-1}$: mm$^{-2}$) of NO by the endothelial cells that line the blood vessels and by blood platelets.

A potentially important strategy for reducing post-operative complications is to provide medical devices comprising an NO-releasing zeolite in accordance with the present invention, thereby mimicking the action of the endothelial cells. The Co-exchanged zeolite-A samples prepared as described previously, in a 75:25 wt % mixture with powdered polytetrafluoroethylene (PTFE) were prepared as mechanically stable pressed disks as follows.

The zeolite was ground with PTFE in the desired ratio (75% zeolite:25% PTFE). The mixture was then pressed into disks (5 mm, ~20 mg) under 2 tons for 30 seconds.

Figure 8:
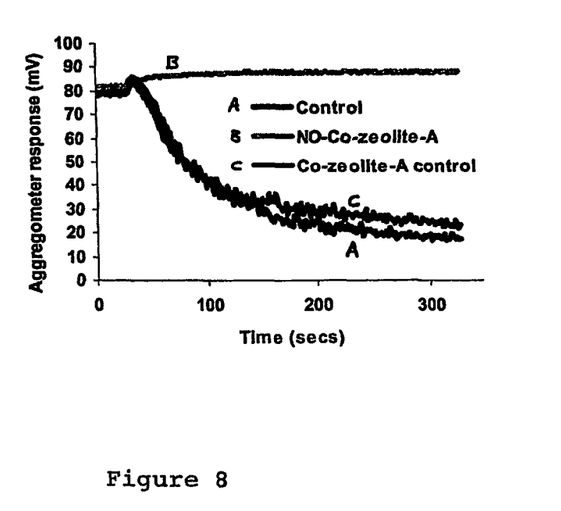
FIG. 8 is a graph showing the aggregometer response over time for the blood platelet aggregation experiments performed in accordance with Example 8.

The disks were then dehydrated and loaded with nitric oxide in the same way as the powder samples. Tests with disks made from only NO-exposed PTFE showed no delivery of nitric oxide. The zeolite/PTFE disks were then suspended in a steel wire holder below the surface of platelet rich plasma (PRP) (prepared as described below) in the cuvette of a four-channel platelet aggregometer at 37° C. After a short induction period (1 minute), platelet aggregation was initiated and then measured as a change in turbidity (light transmission) of PRP against a platelet poor plasma (PPP) blank. The results depicted as a graph in FIG. 8 show that a NO-loaded Co-exchanged zeolite-A/PTFE sample completely inhibits platelet aggregation (line 2) while a Co-exchanged zeolite/PTFE sample that has not been loaded with NO shows no inhibition of aggregation (line 3) when compared to a PRP control where no zeolite or PTFE was added (line 1). This experiment illustrates well the potential of the NO-loaded zeolite-A to inhibit thrombosis in physiological solutions and the possibilities of using the zeolites as NO-releasing components in medical devices, e.g. when blended with polymers such as PTFE.

Preparation of Platelet Rich Plasma

Venous blood was drawn from the antecubital fossa of healthy volunteers (aged 20-40 years) into citrated tubes (0.38% final concentration). Volunteers had not taken any medication known to affect platelet aggregation within the last 10 days. Platelet rich plasma (PRP) was obtained from whole blood by centrifugation (350 g; 20 min; room temperature). Platelet poor plasma (PPP) was obtained by further centrifugation of PRP (1200 g; 5 min; room temperature).

EXAMPLE 9

Antibacterial Action of NO-Containing Zeolites

Between 1 and 10 mg of NO-loaded cobalt exchanged zeolite-A powder were placed in the centre of bacterial cultures (*P. aureginosa* and *E. coli*) grown on agar. After 24 hours the area of bacteria killed was measured. The effectiveness of NO-containing zeolite-A was approximately 2 to 3 times greater than that of C-zeolite-A that was not loaded with NO.

Figure 9A:
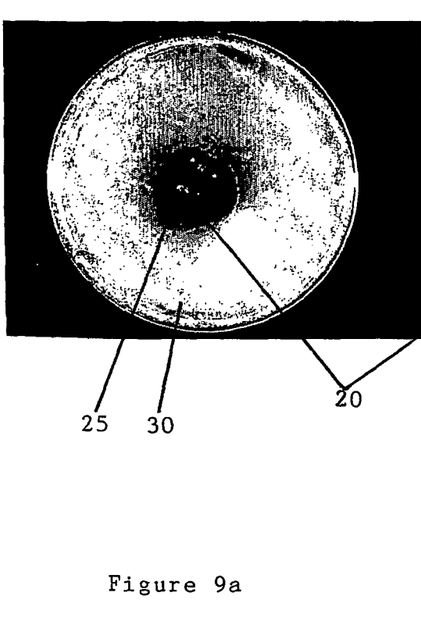
FIGS. 9a and 9b are photographs of bacterial cultures showing the antibacterial action of NO-containing zeolites in accordance with Example 9.
Figure 9B:
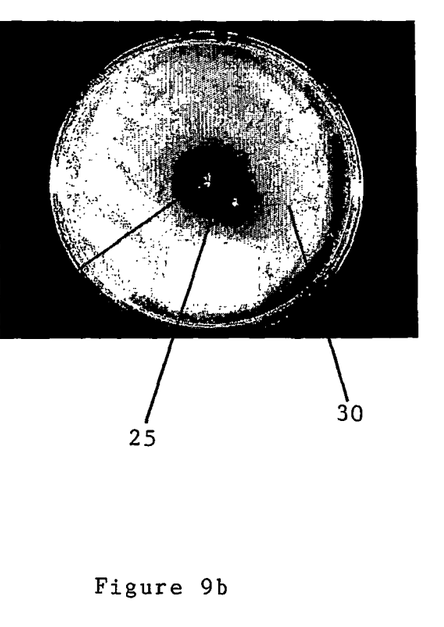

FIGS. 9a and 9b show the anti-bacterial effect of NO-loaded Co-exchanged zeolite-A as dark areas 25 around the power grams 20. The light areas 30 are living bacterial culture. The bacteria used are *P. aureginosa* (FIG. 9a) and *E. Coli* (FIG. 9b).

In summary, the present invention is shown to have application in NO storage and release for biological and medical applications. The preparation and loading of zeolites with nitric oxide is relatively facile, and the NO loaded zeolites are stable when stored in anhydrous conditions at room temperature. The delivery of NO occurs by simple reaction with water, and the amount of nitric oxide released can be tailored by altering both the type and number of metal cations in the zeolite structures. NO-releasing zeolites according to the present invention are shown to inhibit platelet aggregation in physiological fluids, a potentially important application in the prevention of thrombus. The examples hereinabove are not to be construed as limiting on the scope of the present invention, but merely representative embodiments thereof. Other ways of performing the invention will be apparent to the skilled person.

The invention claimed is:

1. A pharmaceutical composition for storage and subsequent release of nitric oxide (NO) for delivery to a human or animal, the composition comprising:
   a partially or fully dehydrated aluminosilicate zeolite and a pharmaceutically acceptable carrier,
   wherein the partially or fully dehydrated zeolite comprises:
   (i) extra-framework cations selected from the group consisting of Ca, Mg, Fe, Cu, Ru, Rh, Co, Ni, Zn and Ag, effective to bind nitric oxide, and (ii) nitric oxide bound to the extra-framework cations, whereby the nitric oxide is released by displacement by moisture upon exposure of the composition to moisture at body or room temperature.

2. The pharmaceutical composition according to claim 1, wherein the extra framework cations are selected from the group consisting of Mg, Fe, Cu, Co, and Ni.

3. The pharmaceutical composition according to claim 1, wherein the extra-framework cations comprise a transition metal.

4. The pharmaceutical composition according to claim 1, wherein the zeolite has an LTA (Linde Type A/Zeolite A) framework structure.

5. The pharmaceutical composition according to claim 4, wherein the zeolite is selected from the group consisting of Ni-LTA(A), Cu-LTA(A), Co-LTA(A), Mg-LTA(A), and Fe-LTA(A).

6. The pharmaceutical composition according to claim 1, in the form of a powder or a monolith.

7. The pharmaceutical composition according to claim 6, wherein the composition is in the form of a monolith comprising a powdered zeolite and a binder.

8. The pharmaceutical composition according to claim 7, wherein the binder is selected from ceramic binders and polymeric binders.

9. The pharmaceutical composition according to claim 8, wherein said ceramic binder is either silica or alumina, and said polymeric binder is selected from the group consisting of polysulfone, polyethylene, polyethylene terephthalate (PET), polystyrene and polytetrafluoroethylene (PTFE).

10. The pharmaceutical composition according to claim 1, in anhydrous form.

11. The pharmaceutical composition of claim 1, wherein the zeolite has a framework structure selected from LTA (Linde Type A/zeolite A), FAU (faujasite), MFI (ZSM-5), MOR (mordenite), FER (ferrierite), BEA (zeolite beta), PHI (zeolite Phi) and SAS (STA-6/St. Andrews Six).

12. The pharmaceutical composition of claim 1, wherein the extra-framework cations are monovalent, divalent or trivalent cations.

13. The pharmaceutical composition of claim 1, wherein the aluminosilicate zeolite possesses an aluminum to extra-framework cation ratio ranging from 1.50 to 17.82.

14. A medical article for storage and subsequent release of nitric oxide for delivery to a human or animal, the medical article selected from the group consisting of wound dressings, bandages and patches and comprising the pharmaceutical composition according to claim 1.

15. The medical article of claim 14, wherein said medical article is a wound dressing.

16. A medical article of claim 14, wherein the pharmaceutically acceptable carrier is a binder that is either a ceramic binder or a polymeric binder and the composition is in the form of a monolith.

17. A sealed airtight package comprising the pharmaceutical composition according to claim 1, whereby, as a result of said packaging, exposure of the pharmaceutical composition to moisture and premature release of nitric oxide is prevented.

18. The sealed airtight package of claim 17, comprising the pharmaceutical composition in anhydrous form.

19. A sealed airtight package comprising the medical article according to claim 14, whereby, as a result of said packaging, exposure of the pharmaceutical composition to moisture and premature release of nitric oxide is prevented.

* * * * *